United States Patent [19]
Nathan et al.

[11] Patent Number: 5,914,390
[45] Date of Patent: Jun. 22, 1999

[54] METHODS FOR INCREASING YIELDS OF RECOMBINANT PROTEINS

[75] Inventors: Ranga Nathan, Danville; Henryk Cudny, Concord, both of Calif.

[73] Assignee: Celtrix Pharmaceuticals, Inc., Santa Clara, Calif.

[21] Appl. No.: 08/855,774

[22] Filed: May 12, 1997

[51] Int. Cl.$^6$ .............................. C07K 1/00; C07K 14/00; C12N 15/00
[52] U.S. Cl. .......................... 530/380; 530/412; 530/419; 530/422; 530/350; 435/69.1
[58] Field of Search .................................. 530/412, 419, 530/422, 380, 350

[56] References Cited

U.S. PATENT DOCUMENTS

| | | | |
|---|---|---|---|
| 4,511,502 | 4/1985 | Builder et al. | 530/417 |
| 4,511,503 | 4/1985 | Olson et al. | 530/422 |
| 4,512,922 | 4/1985 | Jones et al. | 530/408 |
| 4,518,526 | 5/1985 | Olson | 530/351 |
| 4,599,197 | 7/1986 | Wetzel | 530/405 |
| 4,620,948 | 11/1986 | Builder et al. | 530/419 |
| 5,258,287 | 11/1993 | Baxter et al. | 435/69.1 |
| 5,408,038 | 4/1995 | Smith et al. | 530/359 |
| 5,605,691 | 2/1997 | Carroll | 424/184.1 |

FOREIGN PATENT DOCUMENTS

| | | |
|---|---|---|
| 0 114 506 | 8/1984 | European Pat. Off. . |
| 0 295 859 | 12/1988 | European Pat. Off. . |
| WO 90/13310 | 11/1990 | WIPO . |
| WO 94/00557 | 1/1994 | WIPO . |
| WO 94/16720 | 8/1994 | WIPO . |
| WO 96/40722 | 12/1996 | WIPO . |
| WO 96/40736 | 12/1996 | WIPO . |
| WO 96/40784 | 12/1996 | WIPO . |

OTHER PUBLICATIONS

Zardeneta, G. et al., Anal. Biochem., vol. 223, pp. 1–6, 1994.
Kohno, T. et al., Meth. Enzymol., vol. 185, pp. 187–195, 1990.
Marston, F. et al., Meth. Enzymol., vol. 182, pp. 264–276, 1990.
Scopes, R., Protein Purification, 2nd Ed., Chapter 2, pp. 21–40, 1988.
Patent Abstracts of Japan, abstract of Japanese Patent Application Publication No. JP 01320984, "Production of Fructose Dehydrogenase", published Dec. 27, 1989.
Burke et al., "Effect of Polyanions on the Unfolding of Acidic Fibroblast Growth Factor", (1993) *Biochemistry* 32:6419–6426.
Chen et al., "Strategies To Suppress Aggregation of Recombinant Keratinocyte Growth Factor During Liquid Formulation Development", (1994) *Journal of Pharmaceutical Sciences* (1994) 83:1657–1661.
Chen et al., "Stabilization of Recombinant Human Keratinocyte Growth Factor by Osmolytes and Salts", (1996) *Journal of Pharmaceutical Sciences* 85:419–422.
Copeland et al., "Catalytic Subunit of Human DNA Polymerase α Overproduced from Baculovirus–infected Insect Cells", (1991) *Journal Biological Chemistry* 266:22739–22748.
Ron et al., "Expression of Biologically Active Recombinant Keratinocyte Growth Factor" (1993) *The Journal of Biological Chemistry* 268:2984–2986.
Sambrook et al., eds., *Molecular Cloning: A Laboratory Manual*, Cold Spring Harbor Laboratory Press, Cold Spring Harbor, (1989). A title page and table of contents are included herewith.
Ausubel et al., eds., *Current Protocols in Molecular Biology*, John Wiley & Sons, New York, (1993). A title page and table of contents are included herewith.

*Primary Examiner*—Robert A. Wax
*Assistant Examiner*—Peter P. Tung
*Attorney, Agent, or Firm*—Morrison & Foerster LLP

[57] ABSTRACT

Methods are disclosed for increasing the yields of recombinant proteins. Addition of one or more protective agents, such as a sulfated compound (including heparin, heparin sulfate, sodium dodecyl sulfate, and the like), hyaluronic acid or deoxycholate, to recombinant protein production processes is disclosed. Addition of protective agents to the recombinant production process results in increased yields of recombinant proteins.

50 Claims, No Drawings

METHODS FOR INCREASING YIELDS OF RECOMBINANT PROTEINS

BACKGROUND OF THE INVENTION

Recombinant production allows the large scale manufacturing of therapeutic proteins while avoiding the many of the difficulties and hazards of protein purification from natural sources. In the case of human proteins, recombinant manufacturing is frequently the only practical method for producing the amounts of protein required for commercial sales of therapeutic products. Recombinant production also eliminates worker exposure to human fluid and tissues, avoiding potential exposure to infectious agents such as viruses.

Recombinant manufacturing involves the expression of a DNA construct encoding for the desired protein in a recombinant host cell. The host cell can be either prokaryotic (e.g., bacteria such as *Escherichia coli*) or eukaryotic (e.g., yeast or a mammalian cell line). For large scale recombinant manufacturing, bacterial or yeast host cells are most commonly used, due to the ease of manipulation and growth of these organisms and also because these organisms require relatively simple growth media.

Recombinant manufacturing does, however, have its difficulties. Expression constructs must be optimized for the particular protein and for the host cell. Expression of the recombinant protein in the host cell exposes the recombinant protein to a new set of host cell enzymes, such as proteases, which can modify or even degrade the recombinant protein. Modification and degradation of the recombinant protein is, of course, undesirable, as it decreases yields and can complicate the purification of the recombinant protein.

Protamine sulfate is a compound which is well known in the art of recombinant protein production for use in removing undesired DNA from a solution. When protamine sulfate is used to remove undesired DNA, it is added to clarified lysates (i.e., the solution resulting from lysis of the host cells and the removal of cellular debris) at concentrations of about 0.1 to 0.2% (w/v). Addition of protamine sulfate causes the precipitation of DNA, allowing for easy removal by filtration or centrifugation. Addition of protamine sulfate prior to the clarified lysate stage is normally considered undesirable; if protamine sulfate is added prior to the clarified lysate stage, the resulting precipitated DNA can complicate the clarification process (for proteins accumulating in soluble form) or contaminate the "inclusion bodies" (for proteins that accumulate in insoluble form).

Sodium dodecyl sulfate (SDS) is a sulfated detergent that is occasionally used to lyse the membranes of recombinant host cells, particularly for the isolation of large plasmids. The use of SDS in lysing host cells for the recovery of recombinant protein is, however, generally avoided as SDS binds to proteins (normally denaturing them) and can be very difficult to remove.

A number of compounds are available that will increase recombinant protein yields by inhibiting host cell protease activity. Unfortunately, these compounds can be toxic (e.g., phenylmethylsulfonylfluoride(PMSF)), and are, therefore, undesirable for inclusion in a process for manufacturing a product for administration to humans or other living organisms. Other protease inhibitors are available that are not toxic, such as tripeptides, but these compounds are generally so expensive as to render them impractical for inclusion in a commercial manufacturing process.

Accordingly, there is a need in the art for methods that increase the yield of recombinant proteins without the use of toxic or prohibitively expensive compounds.

SUMMARY OF THE INVENTION

In one aspect, the invention discloses methods for improving yields of recombinant proteins by adding one or more protective agents to the recombinant production process. Protective agents are added to host cell suspensions prior to lysis of the host cells. Addition of protective agents to the host cell suspension prevents degradation and/or modification of the recombinant protein during the purification process.

In another aspect, the protective agent(s) is added to clarified lysates from recombinant host cells, thereby increasing yields of the recombinant protein of interest.

In a further aspect, the protective agent is added following solubilization and refolding of the recombinant protein of interest, thereby increasing yields of the recombinant protein of interest.

In a specific embodiment, the recombinant protein of interest is insulin- like growth factor binding protein 3 (IGFBP-3).

DETAILED DISCLOSURE OF THE INVENTION

The inventors have found that protective agents (i.e., sulfated compounds, deoxycholate, and glycosaminoglycans) can improve the yields of recombinant proteins. Addition of protective agents, either as a single agent or in combination, to recombinant protein purification schemes increases the yields of recombinant proteins. The protective agent or agents may be added at any stage of the purification of the recombinant protein. In one preferred embodiment, the protective agent or agents are preferably added prior to the lysis of the recombinant host cells. In another embodiment, the protective agent or agents are added to the purification process at the "clarified lysate" stage (i.e., following the lysis of the host cells and the removal of cellular debris). In a further embodiment, the protective agents are added to the refolding reaction.

As used herein, the term "protective agent" refers to a chemical compound which is a sulfated compound, a glycosaminoglycan, or deoxycholate.

As used herein, the term "sulfated compound" refers to a chemical compound that has at least one sulfate moiety as part of its structure. Sulfated compounds include, but are not limited to, sodium dodecyl sulfate (SDS), chondroitin sulfate (CS), protamine sulfate (PS), heparin (low molecular weight forms of heparin), heparin sulfate (HS), and ammonium sulfate (AS).

As used herein, the term "glycosarninoglycan" refers to chemical compounds that are polysaccharides containing amino sugars. Examples of glycosaminoglycans include CS, heparin, HS, dermatan sulfate, keratan sulfate, and hyaluronic acid.

As used herein, the term "recombinant host cell" refers to host cells that have been engineered to express a desired recombinant protein. Methods of creating recombinant host cells are well known in the art. For example, see Sambrook et al. (MOLECULAR CLONING: A LABORATORY MANUAL (Sambrook et al, eds., Cold Spring Harbor Laboratory Press, Cold Spring Harbor, 1989), Ausubel et al. (CURRENT PROTOCOLS IN MOLECULAR BIOLOGY Ausubel et al., eds., John Wiley & Sons, New York, 1987) or International Patent Application No. WO 96/40722. Preferably, recombinant host cells are constructed according to the disclosure set forth in WO 96/40722.

As used herein, the term "recombinant protein" refers to any protein of interest that can be manufactured using recombinant DNA technology.

Recombinant host cells may be any of the host cells used for recombinant protein production, including, but not limited to, bacteria, yeast, insect and mammalian cell lines. Preferably, the recombinant host cell is bacterial. More preferably, the recombinant host cell is an *Escherichia coli* (*E. coli*) strain, such as *E. coli* strain W3 11 ODE3.

Recombinant host cells may be made by transforming host cells with expression vectors containing DNA coding for the recombinant protein of interest. Recombinant host cells may be transformed by a variety of techniques well known to the art, such as, but not limited to, calcium chloride for bacterial or yeast host cells, calcium phosphate for insect or mammalian host cells, or electroporation may be used for any host cell type. Methods for transformation of recombinant host cells may be found in Sambrook et al. (MOLECULAR CLONING: A LABORATORY MANUAL (Sambrook et al., eds., Cold Spring Harbor Laboratory Press, Cold Spring Harbor, 1989) and Ausubel (CURRENT PROTOCOLS IN MOLECULAR BIOLOGY (Ausubel et al., eds., John Wiley & Sons, New York, 1987)).

Expression constructs containing DNA coding for a recombinant protein of interest may be constructed by standard methods well known to the art. DNA coding for the recombinant protein of interest may be obtained from natural sources, such as genomic or cDNA libraries, or be chemically synthesized. Expression constructs generally comprise control sequences in operable linkage with the DNA coding for the recombinant protein of interest. The control sequences may be naturally occurring in the host (e.g., the lac or trp operons in *E. coli*, the α-mating factor promoter in yeast, or the DHFR promoter in mammalian cells), variants of naturally occurring promoter (e.g., the $lac_{uv5}$ operon or the tac promoter in *E. coli*) or viral promoters (e.g., the T7 promoter). The expression construct may be on a replicable vector, such as a plasmid, cosmid, yeast artificial chromosome and the like, or may be integrated into the chromosome of the recombinant host cell (see, for example, International Patent Application No. 96/40722). Preferably the expression construct is integrated into the recombinant host cell chromosome.

Recombinant host cells are cultured in liquid medium containing assimilatable sources of carbon, nitrogen, and inorganic salts, using methods that are well known to the art. Transformed insect or mammalian cells are cultured in liquid medium containing assimilatable sources of carbon, nitrogen, and inorganic salts, and, optionally, containing vitamins, amino acids, growth factors, and other proteinaceous culture supplements known to the art. Liquid media for culture of host cells may, optionally, contain antibiotics or antifungals to prevent the growth of undesirable microorganisms and/or compounds including, but not limited to antibiotics, to select for host cells containing the expression construct.

The expression construct is preferably inducible (i.e., the addition of a compound to the growth medium induces expression and accumulation of the recombinant protein of interest). A variety of inducible systems are well known in the art. The skilled artisan will select a particular inducible system based on the exact requirements of the recombinant protein of interest, as is standard in the art.

Cultured recombinant host cells containing the recombinant protein of interest may be harvested from the growth media by any technique known in the art, such as filtration or centrifugation. Preferably, the recombinant host cells are collected by centrifugation.

The collected recombinant host cells are then resuspended in a lysis buffer. The exact composition of the lysis buffer will depend on the exact recombinant host cell and the properties of the recombinant protein of interest. A lysis buffer will generally contain a buffering compound to maintain the pH, and may contain a variety of salts, acids, bases, and other compounds, as will be apparent to one of skill in the art. In one embodiment of the instant invention, a protective agent(s) is included in the lysis buffer or added to the lysis buffer following resuspension of the recombinant host cells. This embodiment is preferred when the recombinant protein of interest accumulates within the recombinant host cell in soluble form. Preferably, the protective agent(s) is added to at least 0.01% (w/v). More preferably, the protective agent(s) is added to at least 0.03% (w/v). Addition of the protective agent(s) to the recombinant host cells resuspended in lysis buffer reduces degradation and/or modification of the recombinant protein of interest during the purification process, thereby increasing yields of the purified protein.

Recombinant host cells may be lysed by any method that is known in the art, including sonication, disruption in a microfluidizer, and the like. Preferably, the recombinant host cells are lysed in a microfluidizer.

In the case that the recombinant protein of interest accumulates in the recombinant host cell in soluble form, cellular debris is removed following lysis to render a clarified lysate. Cellular debris may be removed by any method known in the art, such as filtration or centrifugation. Preferably, cellular debris is removed by centrifigation. In another embodiment, protective agent(s) is added to the clarified lysate. Addition of the protective agent(s) to the clarified lysate reduces degradation and/or modification of the recombinant protein of interest during the purification process, thereby increasing yields of the purified protein.

In the case where the recombinant protein of interest accumulates in the recombinant host cell in insoluble form, the recombinant protein of interest must be collected, washed, and resolubilized. Insoluble proteins are generally resistant to degradation and modification, therefore the protective agent(s) need not be added to the purification process until the recombinant protein of interest is solubilized. The collection, washing, and resolubilization of insoluble recombinant protein of interest may be accomplished by any method known in the art, such as those described in U.S. Pat. Nos. 4,518,526, 4,512,922, 4,511,502, 4,511,503, 4,620, 948, or 4,599,197. In a further embodiment, the protective agent(s) is added to the solubilization buffer, prior to the resolubilization of the recombinant protein of interest. This embodiment is preferred when the recombinant protein of interest accumulates in insoluble form in the recombinant host cells. Addition of a protective agent(s) to the solubilization buffer decreases degradation and/or modification of the recombinant protein of interest during and following solubilization, resulting in increased yields of the recombinant protein of interest.

In the case that the recombinant protein of interest accumulates in the cell in a non-native conformation, the recombinant protein of interest must be refolded to its native conformation. Refolding of recombinantly produced protein is well known in the art and generally consists of reducing a solution of denatured protein to break improper disulfide bonds, then adding an oxidizing agent to allow the reformation of intrachain disulfide bonds. The exact refolding protocol will be optimized for each particular protein, as will be apparent to one of the art, although guidance may be found in U.S. Pat. Nos. 4,511,502, 4,511,503, and 4,512,922. In another embodiment, one of the preferred embodiments where the protein of interest accumulates in insoluble form, the protective agent(s) is added to the refolding reaction. The protective agent(s) may be added along with the reducing agent, along with the oxidizing agent, or as a separate additive to the refolding reaction.

Following preparation of the clarified lysate (in the case of proteins which accumulate in soluble form and in native conformation), or refolding (in the case of proteins which accumulate in insoluble form or which accumulate in soluble form with non-native conformation), the recombinant protein of interest may then be further purified. The exact steps and conditions for purification will depend on the exact recombinant protein of interest and the desired use for such protein, as will be apparent to one of skill in the art.

EXAMPLES

Example 1

Various compounds were tested for their ability to protect mature IGFBP-3 from degradation by E. coli cell extracts known to contain degradation activity. E. coli extract was from E. coli strain W3110DE3. E. coli strain W310DE3 was grown, collected by centrifugation, resuspended in a lysis buffer containing 50 mM Tris, pH 8.0, 1 mM ethylenediaminetetraacetate (EDTA), and 5 mM dithiothreitol (DTT), and lysed using a microfluidizer to produce a whole cell extract. The whole cell extract was clarified by centrifugation to produce the source of degradation activity.

Purified mature IGFBP-3 was mixed with E. coli extract with various concentrations of potentially protective compounds. The mixtures were incubated for 2 hours at 37° C., and analyzed by sodium dodecyl sulfate polyacrylamide gel electrophoresis (SDS-PAGE). Heparin, protamine sulfate, sodium dodecyl sulfate (SDS), polyethylene glycol (PEG), tripeptides and deoxycholate were tested in this assay. Heparin was found to protect IGFBP-3 from degradation at concentrations as low as 0.01% (the lowest concentration tested), and demonstrated complete protection of IGFBP-3 from degradation at concentrations of 0.03% and higher. Deoxycholate was protective at 0.1% and higher, with full protection from degradation at 1% and above. Protamine sulfate protected IGFBP-3 from breakdown at concentrations of 0.5% and greater, with complete protection at concentrations of 2% and higher. SDS also protected IGFBP-3 from breakdown at concentrations of 0.5% and higher. PEG and tripeptides (Lys—Tyr—Lys, Gly—Gly—Ala, Gly—Leu—Tyr, Lys—Lys—Lys) showed no protective activity.

Example 2

An E. coli host strain carrying an inducible expression construct coding for the expression of human insulin-like growth factor binding protein 3 (IGFBP-3) was grown in a 10 liter fermenter by batch-fed fermentation, induced to express IGFBP-3, and harvested by centrifugation. The IGFBP-3 expressed by these cells is a fusion protein, incorporating a mutant of E. coli DsbA and a linker sequence between the DsbA and the IGFBP-3 that can be cleaved by human rhinovirus 14 protease 3C (3C protease). The DsbA/IGFBP-3 fusion protein accumulates in the host cells in soluble form.

The host cells were resuspended in a lysis buffer of 50 mM Tris, pH 8.0, 1 mM EDTA, and 5 mM DTT. Three different lysis buffers were used, one containing 0.5% heparin, one containing 0.5% deoxycholate, and one with no additives. Resuspended host cells were lysed using a microfluidizer (Microfluidics Corp., Model 110-F) and the resulting lysate was clarified by centrifugation. Sodium dodecyl sulfate polyacrylamide gel electrophoresis (SDS-PAGE) analysis of clarified lysates indicated higher yields of IGFBP-3 fusion protein in the clarified lysates made with the heparin and deoxycholate-containing lysis buffers, as compared to the clarified lysate made with lysis buffer without additives.

The IGFBP-3 fusion proteins were then further processed by proteolytic removal of the DsbA and linker components of the fusion protein. Clarified lysate from an E. coli strain expressing 3C protease was added to the clarified lysates and the NaCl concentration was adjusted to 1 M. Cleavage was allowed to proceed for a minimum of two hours at room temperature. Following cleavage, the mature IGFBP-3 was collected by centrifugation, and resuspended in a solubilization buffer containing 6 M guanidine hydrochloride (GuHCl), 50 mM Tris, pH 8.0, 20 mM DTT and 4 mM EDTA. Following resolubilization, the mixture was diluted four fold with 50 mM Tris, pH 8.0, and cystamine was added to 5 mM to initiate the refolding reaction. The refolding reaction was run for at least two hours at room temperature.

The refolded mature IGFBP-3 solution was buffer exchanged by dialysis into 20 mM potassium phosphate, pH 7.0, 0.3 M NaCl, and 0.5 M AS (Buffer A), and loaded onto a hydrophobic interaction chromatography (HIC) column (Toyopearl phenyl-650 M). Mature IGFBP-3 was eluted with a buffer of 50 mM sodium acetate, pH 5.5, 0.3 M NaCl, then pooled and loaded onto a Sulfopropyl Sepharose (SP-FF) column (Pharmacia). Purified mature IGFBP-3 was eluted with 50 mM sodium acetate, pH 5.5, 1 M NaCl. Purified mature IGFBP-3 was analyzed by reverse phase high performance liquid chromatography (RP-HPLC), and yields were calculated by integration of peak areas from the chromatograms. Yields of refolded mature IGFBP-3, expressed as milligrams of IGFBP-3 per gram of recombinant host cells, are shown in Table I. These results indicate that heparin and deoxycholate can increase yields of recombinant IGFBP-3. The lower yield from the deoxycholate-containing buffer may be due to a deoxycholate-induced reduction in 3C protease activity during the cleavage step, which would render lower yields of mature IGFBP-3.

TABLE I

| Lysis Buffer Additive | RP-HPLC Peak Area | IGFBP-3 Yield |
| --- | --- | --- |
| None | 129,676 | 1.1 mg/g |
| Heparin | 475,899 | 5.0 mg/g |
| Deoxycholate | 282,306 | 2.6 mg/g |

The present invention has been detailed both by direct description and by example. Equivalents and modifications of the present invention will be apparent to those skilled in the art, and are encompassed within the scope of the invention. The publications, patents, and patent applications cited throughout this disclosure are hereby incorporated by reference herein in their entirety.

We claim:

1. A method for increasing yields of recombinant insulin-like growth factor binding protein 3 (IGFBP-3), comprising:
   adding at least one protective agent selected from the group consisting of heparin, glycosaminoglycans, protamine sulfate (PS), and ammonium sulfate (AS) to a suspension of recombinant host cells, said host cells comprising recombinant IGFBP-3;
   lysing said recombinant host cells; and
   purifying said recombinant IGFBP-3.

2. The method of claim 1 wherein said protective agent is added to a concentration of at least 0.01% (w/v).

3. The method of claim 1 wherein said protective agent is added to a concentration of at least 0.03% (w/v).

4. The method of claim 1 wherein said protective agent is added to a concentration of at least 0.5% (w/v).

5. The method of claim 1 wherein said protective agent is a glycosaminoglycan.

6. The method of claim 5 wherein said glycosaminoglycan is hyaluronic acid.

7. The method of claim 5 wherein said glycosaminoglycan is chondroitin sulfate.

8. The method of claim 1 wherein said protective agent is heparin.

9. A method for increasing yields of recombinant insulin-like growth factor binding protein 3 (IGFBP-3), comprising:
   lysing recombinant host cells comprising recombinant IGFBP-3;
   removing cellular debris from said suspension, thereby forming a clarified host cell lysate;
   adding at least one protective agent selected from the group consisting of sodium dodecyl sulfate (SDS), deoxycholate, heparin and glycosaminoglycans to said clarified host cell lysate; and
   purifying said recombinant IGFBP-3.

10. The method of claim 9 wherein said protective agent is added to at least 0.01% (w/v).

11. The method of claim 9 wherein said protective agent is added to at least 0.03% (w/v).

12. The method of claim 9 wherein said protective agent is added to at least 0.5% (w/v).

13. The method of claim 9 wherein said protective agent is a glycosaminoglycan.

14. The method of claim 13 wherein said glycosaminoglycan is hyaluronic acid.

15. The method of claim 13 wherein said glycosaminoglycan is chondroitin sulfate.

16. The method of claim 9 wherein said protective agent is heparin.

17. The method of claim 9 wherein said protective agent is deoxycholate.

18. The method of claim 9 wherein said protective agent is SDS.

19. A method for increasing yields of recombinant insulin-like growth factor binding protein 3 (IGFBP-3), comprising:
   lysing recombinant host cells comprising recombinant IGFBP-3 which has accumulated in said host cell in insoluble form;
   collecting said insoluble recombinant IGFBP-3;
   solubilizing said insoluble recombinant IGFBP-3 in a solubilizing buffer, said solubilizing buffer comprising at least one protective agent selected from the group consisting of heparin, glycosaminoglycans and ammonium sulfate (AS); and purifying said recombinant IGFBP-3.

20. The method of claim 19 wherein said protective agent is added to at least 0.01% (w/v).

21. The method of claim 19 wherein said protective agent is added to at least 0.03% (w/v).

22. The method of claim 19 wherein said protective agent is added to at least 0.5% (w/v).

23. The method of claim 19 wherein said protective agent is a glycosaminoglycan.

24. The method of claim 23 wherein the glycosaminoglycan is hyaluronic acid.

25. The method of claim 23 wherein said glycosaminoglycan is chondroitin sulfate.

26. The method of claim 19 wherein said protective agent is heparin.

27. The method of claim 19 wherein said protective agent is AS.

28. A method for increasing yields of recombinant insulin-like growth factor binding protein 3 (IGFBP-3), comprising:
   lysing recombinant host cells comprising recombinant IGFBP-3 which has accumulated in said host cell in insoluble form;
   collecting said insoluble recombinant IGFBP-3;
   solubilizing said insoluble recombinant IGFBP-3 in a solubilizing buffer, thereby forming a solution of solubilized IGFBP-3;
   adding at least one protective agent selected from the group consisting of heparin and glycosaminoglycans to said solution of solubilized IGFBP-3; and
   purifying said recombinant IGFBP-3.

29. The method of claim 28 wherein said protective agent is added to at least 0.01% (w/v).

30. The method of claim 28 wherein said protective agent is added to at least 0.03% (w/v).

31. The method of claim 28 wherein said protective agent is added to at least 0.5% (w/v).

32. The method of claim 28 wherein said protective agent is a glycosaminoglycan.

33. The method of claim 32 wherein said glycosaminoglycan is hyaluronic acid.

34. The method of claim 32 wherein said glycosaminoglycan is chondroitin sulfate.

35. The method of claim 28 wherein said protective agent is heparin.

36. The method of claim 28 wherein said protective agent is deoxycholate.

37. A method for preventing degradation and/or modification of insulin-like growth factor binding protein 3 (IGFBP-3), comprising adding a protective agent selected from the group consisting of heparin, glycosaminoglycans, protamine sulfate (PS), and ammonium sulfate (AS) to a suspension of host cells wherein said host cells express IGFBP-3.

38. The method of claim 37 wherein said protective agent is a glycosaminoglycan.

39. The method of claim 38 wherein said glycosaminoglycan is hyaluronic acid.

40. The method of claim 38 wherein said glycosaminoglycan is chondroitin sulfate.

41. The method of claim 37 wherein said protective agent is heparin.

42. A method for preventing degradation and/or modification of insulin-like growth factor binding protein (IGFBP-3) comprising adding a protective agent selected from the group consisting of heparin and glycosaminoglycans to a clarified lysate of host cells, said clarified lysate comprising IGFBP-3.

43. The method of claim 42 wherein said protective agent is a glycosaminoglycan.

44. The method of claim 43 wherein said glycosaminoglycan is hyaluronic acid.

45. The method of claim 43 wherein said glycosaminoglycan is chondroitin sulfate.

46. The method of claim 42 wherein said protective agent is heparin.

47. A method for preventing degradation and/or breakdown of insulin-like growth factor binding protein 3

(IGFBP-3), comprising adding a protective agent selected from the group consisting of sodium dodecyl sulfate (SDS), heparin, and glycosaminoglycans to a refolding reaction comprising IGFBP-3.

48. The method of claim 47 wherein said protective agent is a glycosaminoglycan.

49. The method of claim 48 wherein said protective agent is hyaluronic acid.

50. The method of claim 47 wherein said protective agent is heparin.

* * * * *